United States Patent [19]

Mottus

[11] Patent Number: 4,508,866

[45] Date of Patent: Apr. 2, 1985

[54] POLYMERIC ANTITUMOR AGENT

[75] Inventor: Edward H. Mottus, Ballwin, Mo.

[73] Assignee: Monsanto Company, St. Louis, Mo.

[21] Appl. No.: 540,215

[22] Filed: Oct. 7, 1983

Related U.S. Application Data

[63] Continuation-in-part of Ser. No. 274,596, Jun. 17, 1981, abandoned.

[51] Int. Cl.³ .................. C08K 3/16; C08F 222/06
[52] U.S. Cl. ............................. 524/401; 524/548; 525/327.4; 525/327.6; 525/327.8; 424/78
[58] Field of Search ............... 424/78; 524/401, 548; 525/327.4, 327.6, 327.8

[56] References Cited

U.S. PATENT DOCUMENTS

| | | | |
|---|---|---|---|
| 2,313,565 | 3/1943 | McDowell et al. | 260/78 |
| 2,944,033 | 7/1960 | Goodman | 260/2.1 |
| 3,157,595 | 11/1964 | Johnson et al. | 210/54 |
| 3,224,943 | 12/1965 | Espy | 167/78 |
| 3,275,611 | 9/1966 | Mottus et al. | 260/80.5 |
| 3,794,622 | 2/1974 | Breslow | 260/78.5 |
| 3,998,907 | 12/1976 | DiGiulio | 260/857 L |
| 4,255,537 | 3/1981 | Fields et al. | 525/328 |
| 4,309,413 | 1/1982 | Fields et al. | 525/327.6 |
| 4,397,995 | 8/1983 | Oftedahl et al. | 525/327.4 |

FOREIGN PATENT DOCUMENTS 664322  6/1963  Canada .

OTHER PUBLICATIONS

Breslow, *Pure & Appl. Chem.* 46, 103–113 (1976).
Hodnett et al., *J. Med. Chem.* 21 (7), 652–657 (1978).

*Primary Examiner*—John Kight
*Assistant Examiner*—Kriellion Morgan
*Attorney, Agent, or Firm*—Scott J. Meyer; James W. Williams, Jr.

[57] ABSTRACT

The disclosure relates to pharmaceutically acceptable amide and imide derivatives of low molecular weight copolymers of butyl vinyl ether and maleic anhydride having antitumor activity.

9 Claims, No Drawings

4,508,866

POLYMERIC ANTITUMOR AGENT

BACKGROUND OF THE INVENTION

Cross-Reference to Related Application

This is a continuation-in-part of copending application Ser. No. 274,596, filed June 17, 1981, now abandoned.

This invention relates to pharmaceutically acceptable amide and imide derivatives of low molecular weight copolymers of butyl vinyl ether and maleic anhydride having antitumor activity.

Copolymers of alkyl vinyl ethers and maleic anhydride are known in the art as are the amide and imide derivatives thereof. These are generally high molecular weight resins useful in non-pharmaceutical applications such as binders, coatings, elastomers, paper, textiles and the like products. For example, U.S. Pat. No. 2,313,565 describes the preparation of such resins by the catalyzed polymerization of ethyl vinyl ether and maleic anhydride from which the amide and imide derivatives are then made by further reaction with ammonia or with aliphatic and aromatic amines. U.S. Pat. No. 2,944,033 describes similar such production of amides and imides by ammoniation of copolymers of methyl vinyl ether and maleic anhydride.

Butyl vinyl ethers and maleic anhydride are included in extensive lists of various monomeric components of polymeric materials which can be ammoniated to amides and imides in U.S. Pat. Nos. 3,157,595 and 3,998,907. The disclosed use of these derivatized copolymers is for clarification of water and for preparation of elastomeric products, respectively.

Copolymers of vinyl alkyl ethers and maleic anhydride also are described as useful antitumor agents in Canadian Pat. No. 664,326.

Pharmaceutically active copolymers of divinyl ether and maleic anhydride are known such as those described in U.S. Pat. Nos. 3,224,943 and 3,794,622 and by Breslow in *Pure & Appl. Chem.* 46, 103–113 (1976). However, these polymeric materials are relatively high molecular weight substances of 5000 and greater molecular weight.

Low molecular weight polymeric materials with both amide and imide functionality and having antitumor properties are described in U.S. Pat. No. 4,255,537. The base copolymer is prepared by copolymerization of maleic anhydride and other polycarboxylic anhydrides with alkenes such as ethylene and propylene as distinguished from alkenyl oxides such as vinyl ethers. The base copolymer molecular weight ranges from about 300 to about 1500 and the imide comprises about 5 weight % to about 40 weight % of the derivatized groups.

Hodnett et al., *J. Med. Chem.* 21 (7), 652–657 (1978), describe the antitumor activity of copolymers of isobutyl vinyl ethers and acrylic acid against Sarcoma 180. The disclosed molecular weights from viscosity measurements range from 49,000 to 250,000 (Table II).

DESCRIPTION OF THE INVENTION

It has now been found that certain amide and imide derivatives of low molecular weight copolymers of butyl vinyl ether and maleic anhydride exhibit considerable antitumor activity. These are polymeric materials having average molecular weights less than about 3000 and in which the derivatized groups comprise amide and 0 weight % to about 25 weight % imide.

The antitumor activity has been demonstrated in vitro in the human tumor stem (or progenitor) cell assay (also known as the human tumor cloning assay) and in vitro against the Lewis lung.carcinoma.

The underivatized copolymers are prepared from butyl vinyl ether and maleic anhydride. The base copolymers can be prepared by catalyzed polymerization methods well known in the art. Typically, the butyl vinyl ether is reacted with maleic anhydride in the presence of a free-radical promoting catalyst initiator and a liquid solvent that is a solvent for the reactants and a nonsolvent for the polymeric product. Conventional peroxide type and azo type free-radical promoting polymerization catalysts are suitable for this purpose such as, for example, benzoyl peroxide, t-butyl peroxypivalate, t-butyl peroctoate and azobisisobutyronitrile. A particularly useful catalyst system for the polymerization is the combination of organoboron compounds and organic peroxygen compounds as described in U.S. Pat. No. 3,275,611. Use of a lower trialkylboron such as triethylboron and aliphatic or aryl hydroperoxide such as t-butylhydroperoxide or cumene hydroperoxide, respectively, are especially preferred.

The polymerization reaction can take place in conventional polar or nonpolar solvent media, for example, alkylated aromatic hydrocarbons such as ethyl benzene and ketones such as acetone and methyl ethyl ketone. Tetrahydrofuran (THF) is a particularly suitable choice for the solvent medium. Solution polymerization of monomers in THF at about 30° C. using a triethylboron and t-butyl hydroperoxide initiating system is especially useful and enables the preparation of polymers with non-aromatic end groups. It will be appreciated that certain aromatic free-radical initiators, both through initiation of the polymerization reaction and subsequent termination or telomerization with certain aromatic solvent media, can cause the introduction of various aromatic moieties into the polymeric structure. For example, use of benzoyl peroxide as the free-radical initiator and ethyl benzene as the liquid reaction medium can cause introduction of their respective aromatic moieties into the polymeric structure.

The copolymer preferably contains substantially equimolar quantities of the butyl vinyl ether and maleic anhydride residues as will be obtained by use of about equimolar quantities of the reactant monomers.

Following preparation of the base copolymer, derivatization to the antitumor active amide and imide products is carried out by appropriate ammoniation to form amide and imide derivatives such that from about 0% to about 25% by weight of the derivatized groups are imide groups. Ammoniation can be carried out by reaction with ammonia gas or aqueous ammonium hydroxide or by reaction with ammonia in organic solvent media. Ammoniation will generally result in formation of amide as well as ammonium salt groups. Heating at elevated temperature for an extended period of time to drive off water from the molecule will result in formation of imide groups.

The ammoniation can be conveniently carried out by reaction of anhydrous ammonia with the copolymers in organic solvent media such as, for example, toluene and THF, at temperatures of from about 20° C. to about 50° C. for about 0.5 to about 2 hours and preferably from about 25° C. to about 35° C. for about 0.5 to about one hour. The reaction, which can be initiated at ambient temperature, is exothermic and will cause the temperature to rise. Continued ammoniation will then cause the reaction temperature to return to room temperature after the initial exothermic reaction.

The ammonium salt group which exists in the amide and imide derivatives of the copolymer can be converted to any other pharmaceutically acceptable cationic salt form such as, for example, sodium and potassium. Thus, conversion to illustrative sodium and potassium salt forms can be readily carried out by ion exchange of the ammonium salt with well known Rohm and Haas IRC-120 resin and similar such conventional ion-exchange resins in the sodium and potassium ion forms, respectively.

The molecular weight of the amide and imide derivatized copolymers of the present invention can be estimated in terms of the number average molecular weight or in terms of intrinsic viscosity. The number average molecular weight ($M_n$) of these polymeric materials as determined by Vapor Pressure Osmometry in dimethylformamide (DMF) at 90° C. preferably ranges from about 800 to about 3000. Specific viscosity of a 0.5% solution in THF at 25° C. preferably ranges from about 0.01 to about 0.03 dl/g.

The derivatized copolymer products as prepared above are substantially water-soluble and can be placed into any suitable dosage form for the desired end use. They can be administered to a warm-blooded animal by a variety of parenteral routes, especially intraventously and intraperitoneally. Such administration preferably is in aqueous solution such as in sterile water, physiologically normal saline (0.9% NaCl) and the like sterile injectable forms and can be carried out by suitable reconstitution of solid product. The derivatized copolymer products also can be administered orally in the form of tablets, powders, capsules, elixers and the like dosage forms. The active products can be used in admixture with common solid and liquid fillers, diluents, carriers, suspending agents and adjuvants such as, for example, cornstarch, lactose, talc, stearic acid, magnesium stearate, carboxymethyl cellulose, gelatin, acacia and locust bean gums, alcohol, water, dimethylsulfoxide, vegetable oils and the like pharmaceutically acceptable materials. The liquid oral dosage form also preferably is solid reconstituted in liquid mixture at the time of administration in order to maintain stability of the dual groupings of amide and imide. Dosages can vary widely as will be apparent from the more detailed illustrative examples set forth hereinbelow.

The unique antitumor activity of the copolymer products of this invention has been demonstrated in vivo and in vitro. Thus, in tests for activity against Lewis lung carcinoma implanted subcutaneously in $B6D2F_1$ mice, substantial inhibition of primary tumor growth was observed in animals treated with the copolymer products made in accordance with this invention when administered over a wide range of dosages. The Lewis lung carcinoma is generally recognized as a severely intractable tumor condition against which most known antitumor compounds are ineffective. In these in vivo tests, the copolymer of this invention which employs the butyl vinyl ether and maleic anhydride components exhibited substantially greater activity than a copolymer of ethyl vinyl ether and maleic anhydride.

The activity of the copolymer product of this invention was also demonstrated in vitro in the human tumor cloning assay (also known as the human tumor stem cell assay). This assay was developed primarily by research groups led by Salmon and Von Hoff and is reported in *New Eng. J. Med.* 298, 1321–1327 (1978). According to this assay, human tumor cell suspensions are incubated with the test chemotherapeutic agents for one hour before plating the cells in soft agar. The effects of a particular drug are scored on the basis of the reduction in the number of colonies that grow in comparison with colonies on control plates.

The following detailed examples will further illustrate the invention although it will be appreciated that the invention is not limited to these specific examples. In these examples, Imide % was determined by IR spectrometry substantially as described in U.S. Pat. No. 4,255,537.

EXAMPLE 1

Butyl vinyl ether/Maleic anhydride

Copolymer Derivative

Polymer Preparation

A 500 ml, jacketed resin pot fitted with a mechanical stirrer, $N_2$ inlet and condenser, a rubber septum for addition of the monomer, and a glass stopper was used as the reaction vessel. The resin pot was charged with the following solution: 24.5 g maleic anhydride in 150 ml of ethylbenzene. Water was pumped through the jacket at 30° C.

A second monomer solution consisting of 32 ml (25 g) of butyl vinyl ether, 68 ml ethylbenzene, and 2 ml of cumeme hydroperoxide was mixed with $N_2$ in a 100 ml graduated cylinder. This solution was transferred to a 100 cc syringe attached to a syringe pump and added to the resin pot at about 0.28 ml/min. Addition was completed in 6 hours. Also, 2 ml of triethylborane (1M in THF) was added every hour, during the addition of the butyl vinyl ether, for a total of 12 ml.

At the end of addition, the polymer was collected on a coarse fritted glass funnel, washed with hexane, re-filtered and dried in a vacuum oven at 90° C. overnight.

Yield =33.2 g; sp. visc. (0.5% in THF at 25° C.) =0.032.

Amidation 25 g of the above-prepared polymer was dissolved in 200 ml of THF and transferred to a 100 cc syringe attached to a syringe pump. This solution was added at 10 ml/min to a 500 ml, 4-neck flask. The flask was fitted with a mechanical stirrer, gas dispersion tube, thermowell, and a condenser through which the polymer solution was injected via a small tube into 200 ml of THF in the flask. Anhydrous ammonia was bubbled in throughout the reaction period and produced a small exotherm from the addition of the polymer. After the reaction returned to room temperature (about 2 hours), the amidated polymer was collected on a coarse, fritted glass funnel and dried in a dessicator under vacuum overnight.

Imidation

All of the above amidated polymer was placed in a 500 ml, 4-neck flask containing 250 ml of toluene. The flask was fitted with a mechanical stirrer, thermowell, gas dispersion tube, and a condenser with a Dean-Stark water trap. The slurry was refluxed for 4 hours with anhydrous ammonia bubbling in at a slow rate and any water was captured in the trap. At the end of the imidation the mixture was cooled to room temperature and the polymer filtered onto the glass funnel, washed with hexane, refiltered and dried in a dessicator under vacuum overnight.

Imide = 16%.

The amide-imide polymer was then mixed in about 200 ml of de-ionized water and the pH adjusted to 9.5 with concentrated NH₄OH. This resulted in a solution which was filtered through a 0.2 μ filter and freeze dried prior to submission for pharmaceutical evaluation.

Yield = 23.6 g.

EXAMPLE 2

Samples of the final product prepared for pharmaceutical evaluation in accordance with Example 1 above, were tested at various dosages for their antitumor activity against Lewis lung carcinoma. In this test, $10^6$ Lewis lung carcinoma cells were implanted s.c. in the right flank of $B6D2F_1$ male mice (10 per group). The test products were dissolved in 0.9% NaCl solution and administered i.p. in a volume of 0.5 ml per mouse. Tumors were measured in perpendicular diameters on day 14 and tumor volume was calculated by the formula: length $\times$ width$^2 \times 0.5$. Mean and median tumor volumes were calculated for each treatment group (T) and were compared with untreated controls (C) to obtain a T/C ratio. Table 1 sets forth the results with product of Example 1.

added during the 5 hour reaction period at about 0.008 ml/minute for a total of 2.5 ml.

A second monomer solution consisting of 12 ml (9 g) ethyl vinyl ether, 38 ml THF and 0.5 ml t-butylhydroperoxide was added to the resin pot over the 5 hour reaction period at about 0.16 ml/min. via a 100 cc syringe attached to an infusion pump.

At the end of the reaction period, the polymer was precipitated out into hexane, filtered and dried in a vacuum oven at 90° C. overnight.

Yield = 18.9 g; sp. visc. (0.5% wt/vol in THF at 25° C.) = 0.0199.

17.0 g of the above-prepated polymer was ammoniated by first dissolving it in about 150 ml THF and then adding the resulting solution to 200 ml ammonia-saturated THF in a 500 ml, 4-neck flask. Anhydrous ammonia was bubbled in throughout the reaction period at about 7 ml/minute. The addition produced an exotherm and after returning to room temperature the reaction was terminated. The resulting ammoniated polymer was then filtered and dried in a dessicator under vacuum overnight.

Substantially all of the above ammoniated polymer was refluxed in toluene for 4 hours with a slight bubbling in of anhydrous ammonia during the reaction period in a 500 ml, 4-neck flask equipped with a Dean-

TABLE 1

EVALUATION OF EXAMPLE 1 PRODUCT IN sc LEWIS LUNG CARCINOMA

| Dose (mg/kg. ip qD 1-5) | Wt. Change (gm) Day 7 | Wt. Change (gm) Day 14 | Tumor Growth Inhibition (Day 14) N.P.[a] | Median Volume (mm³) | T/C[b] | Mean Volume (mm³) ± S.D. | T/C[b] |
|---|---|---|---|---|---|---|---|
| 2000 | Toxic | | — | | | 10/10 dead by Day 4 | |
| 800 | −2.8 | +1.9 | 1/4 | 160 | .11 | 144 ± 127[t] | .10 |
| 320 | −1.8 | +3.8 | 2/10 | 320 | .22 | 263 ± 169[t] | .18 |
| 128 | −0.6 | +3.2 | 0/10 | 700 | .49 | 810 ± 592[t] | .56 |
| 51.2 | +0.5 | +2.5 | 0/10 | 1131 | .79 | 1314 ± 646 | .91 |
| 20.5 | +0.7 | +2.6 | 0/10 | 1628 | 1.13 | 1769 ± 778 | 1.23 |
| 8.19 | +1.4 | +2.5 | 0/10 | 1186 | 1.31 | 1842 ± 585 | 1.28 |
| Untreated Controls | +2.0 | +1.7 | 0/10 | 1152 | | 1194 ± 416 | |
| | +2.1 | +2.9 | 0/8 | 1308 | 1437 | 1377 ± 676 | 1444 ± 600 |
| | +2.0 | +2.0 | 0/10 | 1838 | | 1569 ± 681 | |
| | +2.3 | +3.0 | 0/7 | 1775 | | 1699 ± 582 | |

[a]N.P. = mice without palpable tumors on day 14/total
[b]T/C = ratio of tumor volume in treated group relative to untreated controls
[t] = Significantly different from untreated control at p < .01 by Student's t test
qD = daily dosage, days 1 to 5

The surprising and unexpected advantages of the copolymer of this invention which employs a butyl vinyl ether monomeric component is shown by comparison with a copolymer of maleic anhydride and the closely related ethyl vinyl ether. Preparation of the ethyl vinyl ether/maleic anhydride copolymer derivative with 14% imide is shown in Example 3 while preparations of two different copolymers of butyl vinyl ether and maleic anhydride with 16% and 0% imide, respectively, are shown in Examples 1, above, and 4, below. The comparative activity of these polymeric materials against Lewis lung carcinoma is shown in Example 5.

EXAMPLE 3

Ethyl vinyl ether/Maleic anhydride

Copolymer Derivative

Polymer was synthesized by reaction in a 300 ml, jacketed resin pot under nitrogen blanket at 30° C. over a 5 hour period. The resin pot was charged with 12.25 g maleic anhydride and 75 ml THF. Triethylborane was Stark water trap. The solid product was recovered in the same manner as the amide-imide polymer derivative of Example 1.

Imide = 14%.

15 g of the above-prepared amide-imide polymer derivative was mixed with about 150 ml of distilled water and the pH adjusted to 9.5 with concentrated NH₄OH. The resulting solution was filtered through a 0.22 μ filter and freeze dried prior to submission for pharmaceutical evaluation.

Yield = 14.4 g.

Analysis: C = 49.9%, H = 7.45%, N = 12.11%.

EXAMPLE 4

Butyl vinyl ether/Maleic Anhydride

Copolymer Derivative

Polymer was synthesized by reaction in a 500 ml, jacketed resin pot under nitrogen blanket at 80° C. over a 5 hour period. The resin pot was charged with 24.5 g maleic anhydride and 150 ml ethylbenzene.

A second monomer solution consisting of 32.2 ml (25 g) butyl vinyl ether, 75 ml ethylbenzene and 2.0 g 2,2'-azobis[2-methylpropionitrile]was added to the resin pot over the 5 hour reaction period at about 0.25 ml/minute via a syringe attached to an infusion pump.

At the end of the reaction period, the polymer was collected on a glass fritted filter, washed with hexane and dried in a vacuum oven at 90° C. overnight.

Yield =35.3 g; sp. visc. (0.5% in THF at 25° C.) =0.0191; sp. visc. (1.0% in THF at 25° C.) =0.054.

12 g of the above-prepared polymer was ammoniated by dissolving in about 100 ml THF and adding the resulting solution at the rate of about 5 ml/minute to anhydrous ammonia-saturated THF (200 ml) in a 500 ml, 4-neck flask. The addition produced an exotherm and after returning to room temperature the reaction was terminated. The resulting ammoniated polymer was filtered and dried in a dessicator under vacuum overnight.

Imide =0%.

The above-prepared amidated polymer derivative was dissolved in about 150 ml distilled water and the pH was adjusted to 9.5 with concentrated $NH_4OH$. The resulting solution was filtered through a 0.22 $\mu$ filter and freeze dried prior to submission for pharmaceutical evaluation.

Yield =13.0 g.

EXAMPLE 5

Samples of the final products prepared for pharmaceutical evaluation in accordance with Examples 1, 3 and 4, above, were tested at various dosages for their antitumor activity against Lewis lung carcinoma substantially in accordance with the procedure set forth in Example 2, above. The following Table 2 sets forth the dosages used and the T/C ratio obtained in these tests and compared with controls in male $B6D2F_1$ mice.

TABLE 2

| Dose | T/C | | |
|---|---|---|---|
| mg/kg | Ex. 1 | Ex. 3 | Ex. 4 |
| 2000 | Toxic | 0.31 | Toxic |
| 800 | 0.11 | 0.52 | 0.03 |
| 320 | 0.22 | 1.03 | 0.06 |
| 128 | 0.49 | 0.75 | 0.13 |
| 51 | 0.79 | 0.76 | 0.38 |
| 20 | 1.13 | 0.79 | 0.48 |
| 8 | 1.31 | 0.79 | 0.86 |

It is seen from the above that in the wide dosage range of from 128 to 800 mg/kg, the copolymers with the butyl vinyl ether component (Examples 1 and 4) are from about 1½ to 17 times as active as the copolymer with the ethyl vinyl ether component (Example 3) in the Lewis lung carcinoma assay.

The impressive advantages of the aforesaid copolymer products of this invention are further shown by comparing the median effective dose (ED50) of the copolymer against the Lewis lung carcinoma with that of the copolymer of ethyl vinyl ether and maleic anhydride. In this comparison, a corresponding copolymer of ethylene and maleic anhydride deivatized with amide and imide groups as described in U.S. Pat. No. 4,255,537, with an ED50 =1, was used as a control. The activity of the latter compound against the Lewis lung carcinoma is described by Fields et al., *J. Med. Chem.* 25 (9), 1060-1064 (1982). The ED50 was calculated by determining the equation for the best fit straight line of the % inhibition (in the above Lewis lung carcinoma assay), vs. the logarithm of the dose plot for the sample product. The logarithm of the doses at which 50% inhibition would be predicted from the plot were then calculated and the ED50 indices determined from these values. (See *Remmington's Pharmaceutical Sciences*, Mack Publishing Co., 15th Edition, 1975, page 671, for background on the ED50 method.) ED50 values greater than one represented substances which were more active than the control product.

The followin Table 4 sets forth the ED50 values for these polymeric products.

TABLE 4

| Polymer Product | ED50 |
|---|---|
| Ex. 1 | 2.5 |
| Ex. 3 | 0.2 |
| Ex. 4 | 10.0 |
| Control | 1 |

Ex. 1 and 4 are copolymers of butyl vinyl ether/maleic anhydride.
Ex. 3 is copolymer of ethyl vinyl ether/maleic anhydride.
Control is copolymer of ethylene/maleic anhydride.
All products derivatized to amide/imide/ammonium salt except Example 4 derivatized to amide/ammonium salt.

The antitumor activity of the copolymer products of this invention also was demonstrated in a standard human tumor cloning assay. In this assay, the copolymer products were tested at a concentration of 1, 0.1 and 0.01 $\mu$g/ml. A one hour exposure was utilized against 21 different human tumors grown in a human tumor cloning system. Results which show less than 50% survival of the tumor colony forming units (TCFU's) growing in a layer of nutrient medium and soft agar incubated at 37° C. for ten days confirm antitumor activity of the test sample.

The following Table 5 sets forth the number of tumor specimens showing this survival rate ($\overline{c}<50\%$) out of 21 evaluated specimens at the 1 $\mu$g/ml concentration for the copolymer product of Example 4.

TABLE 5

| Polymer Product | Tumor Specimens Survivors/Evaluated |
|---|---|
| Ex. 4 | 5/21 |

Various other examples will be apparent to the person skilled in the art after reading the instant disclosure without departing from the spirit and scope of the invention and it is intended that all such examples be included within the scope of the appended claims.

What is claimed is:

1. An antitumor active, water-soluble composition of matter selected from the group consisting of low molecular weight copolymers of butyl vinyl ether and maleic anhydride, wherein said molecular weight is less than about 3000 and wherein said copolymer is derivatized to contain half-amide, half-carboxyl acid groups in which from 0 weight percent to about 25 weight percent of the half amide, half-carboxyl acid groups are converted to imide groups, and the pharmaceutically acceptable cationic salt derivatives of said derivatized copolymers.

2. The composition of matter of claim 1 in which the derivatized groups are half-amide, half-ammonium salt and imide groups.

3. The composition of matter of claim 1 in which the derivatized groups are half-amide, half-ammonium salt groups.

4. A pharmaceutical composition having antitumor activity which comprises, as active ingredient, the copolymer derivative of claim 1, in association with a significant amount of a pharmaceutically acceptable carrier.

5. A pharmaceutical composition having antitumor activity which comprises, as active ingredient, the copolymer derivative of claim 2, in association with a significant amount of a pharmaceutically acceptable carrier.

6. A pharmaceutical composition having antitumor activity which comprises, as active ingredient, the copolymer derivative of claim 3, in association with a significant amount of a pharmaceutically acceptable carrier.

7. A pharmaceutical composition for parenteral administration and useful for the treatment of tumors which comprises, as active ingredient, the copolymer composition of claim 1, in association with a significant amount of a sterile injectable pharmaceutically acceptable carrier.

8. A pharmaceutical composition for parenteral administration and useful for the treatment of tumors which comprises, as active ingredient, the copolymer composition of claim 2, in association with a significant amount of a sterile injectable pharmaceutically acceptable carrier.

9. A pharmaceutical composition for parenteral administration and useful for the treatment of tumors which comprises, as active ingredient, the copolymer composition of claim 3, in association with a significant amount of a sterile injectable pharmaceutically acceptable carrier.

* * * * *